United States Patent

Galey et al.

Patent Number: 5,760,037
Date of Patent: Jun. 2, 1998

[54] DERIVATIVES OF N'N'-DI(ARALKYL)-N,N'-DI(2-AZAARALKYL)ALKYLENE DIAMINE AND THE USE THEREOF IN PHARMACEUTICAL AND COSMETIC COMPOSTIONS

[75] Inventors: Jean-Baptiste Galey, Aulnay-Sous-Bois; Jacqueline Dumats, Villepinte, both of France

[73] Assignee: L'Oreal, Paris, France

[21] Appl. No.: 681,414

[22] Filed: Jul. 23, 1996

[30] Foreign Application Priority Data

Jul. 26, 1995 [FR] France .................. 95 09118

[51] Int. Cl.$^6$ .............. A61K 31/53; A61K 31/505; C07D 251/42; C07D 239/42
[52] U.S. Cl. .............. 514/245; 424/59; 424/401; 514/275; 514/340; 514/352; 514/365; 514/381; 514/394; 514/397; 544/212; 544/296; 544/331; 544/332; 546/264; 548/190; 548/193; 548/251; 548/252; 548/305.4; 548/335.1
[58] Field of Search .............. 544/212, 296, 544/331, 332; 546/264; 548/190, 193, 251, 252, 305.4, 335.1, 558; 514/245, 275, 340, 352, 365, 381, 394, 397, 422; 424/59, 401

[56] References Cited

U.S. PATENT DOCUMENTS 5,182,387 1/1993 Freedman et al. .......... 540/590

FOREIGN PATENT DOCUMENTS

94/11338 5/1994 WIPO.

OTHER PUBLICATIONS

CA116:74844, 1991.
CA90:186861, 1978.
CA70:37712, 1968.
Inorg. Chem. 1994, 33, 1907–1914.
Journal of Organometallic Chemistry, 497 (1995) 73–79.
Rieger, et al: "Synthesis of chiral and $C_2$-symmetric iron(II) and coblalt(II) complexes bearing a new tetradentate amine ligand system", Journal of Organometallic Chemistry, vol. 497 (1995) pp. 73–79.

Primary Examiner—Yogendra N. Gupta
Attorney, Agent, or Firm—Nixon & Vanderhye, P.C.

[57] ABSTRACT

These compounds correspond to the following general formula:

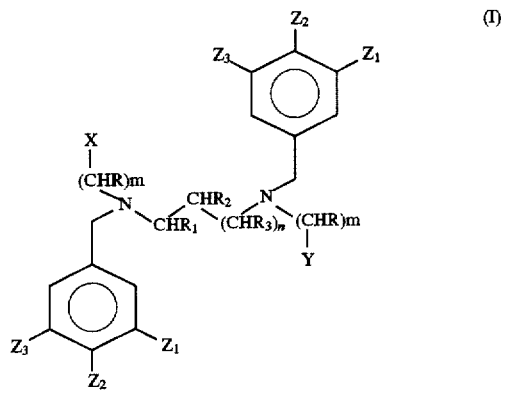

where:

n is 0, 1, or 2, m is are 1, 2, or 3, $R$, $R_1$, $R_2$, and $R_3$, whether identical or different, represent an atom of hydrogen or a linear or branched alkyl radical at $C_1$–$C_4$, $R_1$ and $R_2$, or $R_2$ and $R_3$ taken together can form a 5- or 6-group cycle, X and Y, whether identical or different, represent a nitrogenous aromatic heterocycle in position 2, $Z_1$, $Z_2$, and $Z_3$, whether identical or different, represent an atom of hydrogen, a linear or branched alkyl radical at $C_1$–$C_4$, the radical —$OR_4$ or —$NR_4R'_4$, $R_4$ and $R'_4$ represent an atom of hydrogen or a linear or branched alkyl radical at $C_1$–$C_4$, and the metallic salts and complexes thereof.

Use in pharmaceutical and cosmetic compositions to protect the organism from oxidizing stress situations linked to certain pathological states.

10 Claims, No Drawings

DERIVATIVES OF N'N'-DI(ARALKYL)-N,N'-DI(2-AZAARALKYL)ALKYLENE DIAMINE AND THE USE THEREOF IN PHARMACEUTICAL AND COSMETIC COMPOSTIONS

The present invention claims priority from FR 95 09118, filed Jul. 26, 1995, the entire contents of which are incoprorated herein by reference.

The present invention concerns new derivatives of N,N'-di(aralkyl)-N,N'-di(azaaralkyl) alkylene diamine, which are used in pharmaceutical and cosmetic compositions to protect the organism against oxidizing stress.

In a number of physiopathological and pathological situations, oxidizing stress is defined as a disequilibrium of the antioxidant-prooxidant balance. This disequilibrium triggers uncontrolled oxidative processes within living tissues, these processes involve oxygenated free radicals and lead, in particular, to oxidative damage on biological molecules and macromolecules.

A number of physiopathological situations cause, promote, accompany, or are the direct consequence of an oxidizing stress, including, most notably, inflammation, aging, exposure to ultra-violet rays and ionizing radiation, carcinogenesis, cases of reperfusion ischemia, toxicity and/ or the mode of action of certain drugs.

It has been shown that, during oxidizing stress, iron is released from its habitual storage sites as ferritin, and can then take part in certain reactions, in particular the Fenton and Haber-Weiss reactions, which form hydroxyl radicals known to be responsible for extensive oxidative damage.

To ensure protection against hydroxyl radicals, proposals have been made to use molecules such as D-mannitol, benzoic acid, or DMSO, which can trap hydroxyl radicals. However, hydroxyl radicals are especially reactive, and relatively large quantities of these trapping agents must be used in order to compete with all biological molecules representing potential targets of hydroxyl radicals, a use which raises certain difficulties as a result of the problems of toxicity posed by these trapping agents.

Furthermore, to ensure protection against hydroxyl radicals, a proposal has been made to use iron chelating agents, in particular deferoxamine or diethylene triamine pentacetic acid (DTPA) in order to prevent iron from taking part in the Fenton and Haber-Weiss reactions.

Nevertheless, most of these chelating agents are relatively toxic and can interfere with iron metabolism and chelate the iron of the active sites of certain enzymes or hemoproteins, such as hemoglobin.

Patent Application No. WO 94/11338 proposes the use of certain compounds capable of forming complexes with iron, whose stability constants are low, thereby reducing the risks of toxicity associated with the use thereof.

Following new research on substances which act in accordance with a comparable mechanism, the synthesis of a new class of compounds exhibiting improved biological availability was successfully achieved, a phenomenon which, until now, could not be obtained using iron chelating agents according to prior art.

It was discovered, moreover, that these new compounds formed, in conjunction with iron, complexes whose association constants were lower than those of known chelating agents, such as deferoxamine. Furthermore, the toxicological risks decreased to the extent that, for thermodynamic reasons, they could not displace the iron from the transferrin.

In addition, the oxidation-reduction potential of the iron in the compounds according to the invention is such that they can be reduced using physiological reductants capable, in reduced form, of reacting with hydrogen peroxide to form hydroxyl radicals that are immediately trapped in quasi-stoichiometric fashion by means of an intramolecular aromatic hydroxylation process before they can attack other molecules.

Following intramolecular hydroxylation, these compounds possess an aromatic hydroxy residue capable of occupying a fifth or sixth iron-coordination site. Given the high degree of affinity of phenolate residues for ferric iron, this has the effect of increasing the stability of the complexes by several orders of magnitude and of preventing the subsequent participation of iron in catalysis causing oxidative damage.

The present invention thus concerns, under the heading of new compounds, derivatives of N,N'-di(aralkyl)-N,N'-di (2-azaaralkyl) alkylene diamine, which can be represented for the following general formula:

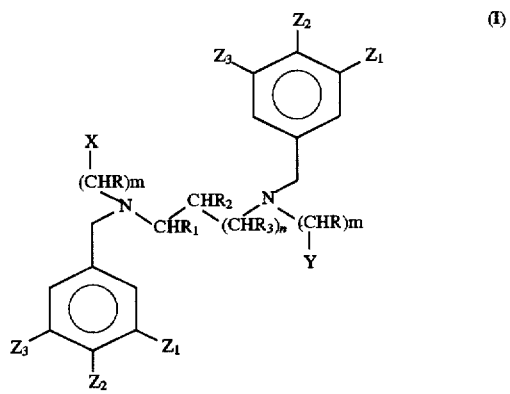

where:
n is 0, 1, or 2,
m is 1, 2, or 3,
$R$, $R_1$, $R_2$, and $R_3$, whether identical or different, represent an atom of hydrogen or a linear or branched alkyl radical at $C_1$–$C_4$,
$R_1$ and $R_2$, or $R_2$ and $R_3$ taken together can form a 5- or 6-membered ring,
X and Y, whether identical or different, represent a nitrogenous aromatic heterocycle
$Z_1$, $Z_2$, and $Z_3$, whether identical or different, represent an atom of hydrogen, a linear or branched alkyl radical of $C_1$–$C_4$, the radical —$OR_4$ or —$NR_4R'_4$,
$R_4$ and $R'_4$ represent an atom of hydrogen or a linear or branched alkyl radical of $C_1$–$C_4$.
and the salts and metallic complexes thereof.

The expression "linear or branched alkyl radical of $C_1$–$C_4$" signifies radicals such as methyl, ethyl, isopropyl, and tert-butyl radicals.

When $R_1$ and $R_2$ or $R_2$ and $R_3$ taken together form a 5- or 6-membered ring, this ring is a potentially-substituted cyclopentyl or cyclohexyl cycle.

When X and Y, whether identical or different, represent a nitrogenous aromatic heterocycle, the latter may be a 2-pyridyl, 2-pyrimidyl, 4-pyrimidyl, 2-triazinyl, 2-imidazolyl, 2-pyrrolyl, 2-tetrazolyl, 4-thiazolyl, 2-methyl-4-thiazolyl, or 2-benzoimidazolyl radical.

According to a first preferred embodiment of the compounds according to the invention, the radicals $Z_1$, $Z_2$, and $Z_3$ are electron-donor groups and preferably represent at least one methoxy group.

Among the salts of the compounds corresponding to formula (I), mention may be made of salts incorporating the addition of a mineral acid such as sulfuric acid, chlorhydric acid, nitric acid, or phosphoric acid.

Among the complexes, mention may be made of those formed by adding zinc chloride or calcium chloride.

As examples of compounds representing compounds corresponding to formula (I), mention may be made of:

N,N'-bis-(3,4,5-trimethoxybenzyl)-N,N'-bis-(2-tetrazolyl-1-ethyl) ethylenediamine, N,N'-bis-(3,4,5-trimethoxybenzyl)-N,N'-bis-(2-pyridyl methyl) ethylenediamine, N,N'-bis-(2-methyl-thiazole-4-ylmethyl)-N,N'-bis-(3,4,5-trimethoxybenzyl) ethylenediamine, N,N'-bis-(1H-benzimidazole-2-ylmethyl)-N,N'-bis-(3,4,5-trimethoxybenzyl) ethylenediamine.

The present invention also concerns the process for preparation of compounds corresponding to general formula (I), which may be represented by the following reaction diagram:

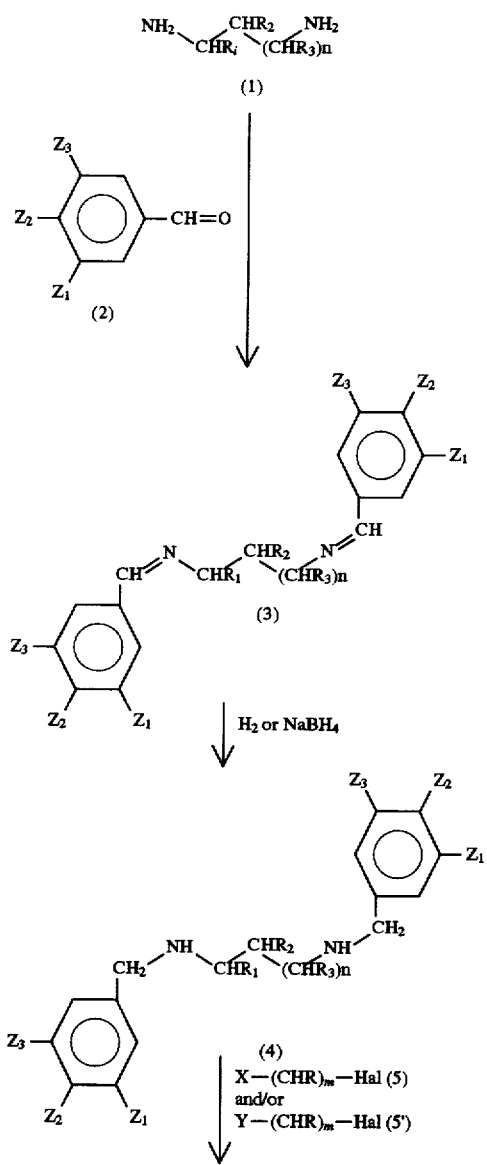

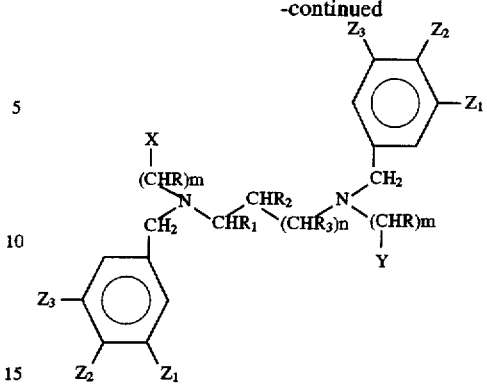

The procedure according to the invention consists in reacting an alkylene diamine corresponding to formula (1) with an aromatic aldehyde corresponding to formula (2) in an organic solvent medium at a temperature below the boiling point of the solvent. The diimine (3) obtained, whether or not it is isolated, is then reduced in the presence of a sodium borohydride or by catalytic hydrogenation, in order to yield diamine corresponding to formula (4).

The diamine (4) is then treated in a basic medium, for example in the presence of sodium carbonate, using a halogenated compound corresponding to formula (5) and/or (5') (Hal being preferably an atom of chlorine or bromine).

After extraction and drying, a compound corresponding to general formula (I) is obtained.

The present invention further concerns a cosmetic or pharmaceutical composition containing at least one compound corresponding to formula (I) or one of the metallic salts or complexes thereof in a cosmetically- or pharmaceutically-acceptable vehicle.

In these compositions, the active compound corresponding to formula (I) is normally present in a proportion of 0.001 to 10% by weight of the total weight of the composition.

The cosmetic compositions may exist in various conventional forms, such as ointments, creams, pomades, gels, sprays, lotions, emulsions, and vesicular dispersions.

It was found, moreover, that, in the compositions according to the invention, the compound corresponding to formula (I) produced a high level of antioxidant activity and, accordingly, allowed them to be protected from oxidation.

When the compound corresponding to formula (I) is used as part of a pharmaceutical treatment, administration may be made orally, topically, or parenterally, the pharmaceutically-acceptable base depending on the type of administration chosen. Doses normally range between 1 mg and 1,000 mg/kg/day.

The pharmaceutical compositions according to the invention are most especially intended to treat oxidant stress conditions linked to certain pathological states, and, in particular, neuro-degenerative disorders such as Parkinson's disease, chronic inflammations, reperfusion ischemia syndrome, the toxicity of some drugs, e.g., certain xenobiotics, and iron overloads.

In the compositions according to the invention, the compound corresponding to formula (I) may, in accordance with a preferred embodiment, be combined with at least one other active substance (or other anti-free radical substance). These substances may be chosen more especially from:

anti-lipoperoxidants, such as vitamin E, trolox, and BHT (butyl hydroxytoluene), biological reductants, such as reduced glutathion and the derivatives thereof, vitamin C and the derivatives thereof, singlet oxygen quenchers, such as β-carotene, systems capable of decomposing hydrogen peroxide, and, in particular, enzymes such as catalase or peroxidases in the presence of their co-substrates, superoxide anion-protection systems, such as superoxide dismutase (SOD) or SOD-like systems, such as Mn-deferal or copper di-isopropyl salicylate, systems capable of decomposing organic hydroperoxides such as glutathion peroxidase, or selenium-based systems.

The compounds corresponding to formula (I) and the active substances or anti-free radical substances such as those specified above may be combined within the same composition, or they may be applied separately.

The following examples are provided in order to illustrate the process for preparation of compounds corresponding to formula (I) and the use thereof in the pharmaceutical and cosmetic fields.

EXAMPLES OF COMPOUND PREPARATION

EXAMPLE 1

Preparation of N,N'-bis-(3,4,5-trimethoxybenzyl)-N, N'-bis-(2-pyridyl methyl) ethylenediamine 1) In a 1-liter three-necked flask, 50 g 3,4,5-trimethoxybenzaldehyde was placed in suspension at ambient temperature in 300 ml methanol. The mixture was heated at 40° C. in order to obtain complete dissolution, and 8.5 ml ethylenediamine were dripped in. The mixture was then allowed to return to ambient temperature. The clear yellow reactive medium obtained after diamine addition rapidly became heterogenous with precipitation of the diimine. The mixture was then stirred for one hour at ambient temperature, before cooling to 5° C. The precipitate was collected by filtration on sintered glass and washed abundantly in cold methanol, then put back in suspension in iced methanol and filtered to remove any trace of residual aldehyde. The white precipitate (49 g) was then dried under a vacuum in the drier (F=148° C.).

2) In a 1-liter three-necked flask, 20 g of the diimine obtained in step 1) were placed in suspension in 400 ml absolute ethanol. Next, 2.27 g sodium borohydride in pellet form were added and the mixture was heated to 55°–60° C. After about 45 minutes, the reactive medium became clear. The mixture was kept for 2 hours at 55°–60° C., then allowed to return slowly to ambient temperature and hydrolyzed using an aqueous 6N HCl solution, until a pH <1 was reached. The reactive medium became yellow, then a precipitate rapidly formed. The mixture was then cooled to +5° C. for about 1 hour while stirring lightly. The precipitate was filtered on sintered glass and washed using absolute ethanol, before being dried in a vacuum in a drier. The N,N'-bis(3, 4,5-trimethoxybenzyl) ethylenediamine dichlorhydrate obtained was used in that state in the final step.

3) 2 g N,N'-bis-(3,4,5-trimethoxybenzyl) ethylenediamine dichlorhydrate obtained above in step 2) were solubilized in 30 ml water. The pH of the solution was brought to 11 using soda solution. A solution containing 1.35 g 2-picolyl chloride were added all at once to 15 ml water. The mixture was heated for 4 hours to 40° C. while keeping the pH at between 10 and 11 by adding a soda solution. The medium was then extracted using 3 times 25 ml dichloromethane, then the organic phase was washed in water saturated with NaCl. After drying and dry-evaporating, 1.6 g of a brown oil were obtained. This oil was purified by chromatography on a silica column (dichloromethane/methanol eluant). 1.4 g of N,N'-bis-(3,4,5-trimethoxybenzyl)-N,N'-bis-(2-pyridyl methyl) ethylenediamine in the form of an oil (yield=57%). The latter was then crystallized, thus producing a white solid having a melting point of 106° C., whose NMR$^1$H spectrum (400 MHZ), mass spectrum, and ultimate analysis matched the expected structure.

|  | C | H | N | O |
|---|---|---|---|---|
| Calculated % (with 0.2 H$_2$O) | 67.37 | 7.00 | 9.25 | 16.38 |
| Found % | 66.95 | 6.96 | 9.19 | 16.26 |

EXAMPLE 2

Preparation of N,N'-bis-(2-methyl-thiazole-4-ylmethyl)-N,N'-bis-(3,4,5-trimethoxybenzyl) ethylenediamine To prepare this compound, the first two steps 1) and 2) in Example 1 were repeated.

3) 1.5 g N,N'-bis-(3,4,5-trimethoxybenzyl) ethylenediamine dichlorhydrate were solubilized in 30 ml of a 1:1 ethanol/water mixture. The pH of the solution was brought to 11 using a soda solution. A solution of 1.25 g 4-chloromethyl-2-methylthiazole in solution in 10 ml water were added all at once. The mixture was heated for 5 hours at 45° C., while maintaining the pH at between 10 and 11 by adding a soda solution. After cooling, the ethanol was evaporated under a vacuum and the mixture was acidified to a pH of 1 using concentrated HCl. Extraction was carried out using 3×25 ml dichloromethane, then the organic phase was dried and dry-evaporation effected. The oil obtained was taken up in 10 ml ethanol +0.5 ml concentrated HCl. The resultant precipitate was filtered and washed in ethylic ether. The solid was then recrystallized in 20 ml isopropanol containing 1% water. In this way, 600 mg of a white powder having a melting point of 190° C. was obtained, whose proton NMR spectrum (400 MHZ) and ultimate analysis matched the expected structure (existing as a dichlorhydrate).

|  | C | H | N | O | S | Cl |
|---|---|---|---|---|---|---|
| Calculated % (with 0.35 H$_2$O) | 53.24 | 6.20 | 7.76 | 14.09 | 8.87 | 9.84 |
| Found % | 53.53 | 6.19 | 7.75 | 14.18 | 8.66 | 9.82 |

EXAMPLE 3

Preparation of N,N'-bis-(1H-benzoimidazole-2-ylmethyl)-N,N'-bis-(3,4,5-trimethoxybenzyl) ethylenediamine To prepare this compound, the first two steps 1) and 2) in Example 1 were first carried out.

3) 1.5 g N,N'-bis-(3,4,5-trimethoxybenzyl) ethylenediamine dichlorhydrate were solubilized in 30 ml 1:1 ethanol/water mixture. The pH of the solution was brought to 11 using a soda solution. A solution of 1.1 g 2-chloromethyl benzimidazole in solution in 30 ml ethanol was added all at once. The mixture was heated for 5 hours at 45° C. while keeping the pH at between 10 and 11 by adding a soda solution. After cooling, the ethanol was evaporated in a vacuum, and the medium was cooled to 0° C. The precipitate formed was filtered and washed with water. The solid was taken up in 15 ml water +0.5 ml concentrated HCl, then filtered and washed in water. The solid was then recrystallized in 10 ml of a 98:2 water/ethanol mixture. 350 mg of a white powder having a melting point of 150° C. (dec.) were obtained, whose proton NMR spectrum (400 MHZ) and ultimate analysis matched the expected structure (in the form of dichlorhydrate).

|  | C | H | N | O | Cl |
|---|---|---|---|---|---|
| Calculated % (with 3.5 H$_2$O) | 55.88 | 6.50 | 10.29 | 18.63 | 8.70 |
| Found % | 55.46 | 6.61 | 10.31 | 18.75 | 8.36 |

EXAMPLE OF PHARMACEUTICAL COMPOSITION

EXAMPLE A

A drinkable suspension according to the invention was prepared by mixing the following constituents:

| | |
|---|---|
| N,N'-bis-(3,4,5-trimethoxybenzyl-N,N'-bis-(2-pyridyl methyl)-ethylenediamine (compound in Example 1) | 0.10 g |
| 90% ethanol | 1.00 g |
| 70% sorbitol | 0.50 g |
| Sodium saccharinate | 0.01 g |
| Preservative | 0.04 g |
| Flavoring qs | |
| Purified water qsp | 5 ml |

This drinkable composition, administered 1 to 2 times a day for at least 3 to 5 weeks, effectively treats most neurodegenerative diseases.

In this drinkable solution, the compound according to Example 1 may be advantageously replaced using the same quantity of one of the compounds in Examples 2 and 3.

EXAMPLE OF COSMETIC COMPOSITION

EXAMPLE B

An oil-in-water emulsion was prepared in accordance with the invention by mixing the following ingredients:

| | |
|---|---|
| N,N'-bis-(3,4,5-trimethoxybenzyl)-N,N'-bis-(2-pyridyl methyl)ethylenediamine (compound in Example 1) | 0.50% |
| Jojoba oil | 13.00% |
| Potassium sorbate | 0.30% |
| Cyclopentadimethylsiloxane | 10.00% |
| Stearyl alcohol | 1.00% |
| Stearic acid | 4.00% |
| Polyethylene glycol stearate | 3.00% |
| Vitamin E | 1.00% |
| Glycerol | 3.00% |
| Preservative | 0.05% |
| Water qsp | 100.00% |

When applied regularly once per day, preferably in the evening, this composition makes it possible to prevent skin aging in an especially significant way. Moreover, it was found that the composition had excellent stability over time and that the active compound allowed protection against oxidative phenomena.

In this composition, the compound in Example 1 may advantageously be replaced by the same quantity of one of the compounds in Examples 2 and 3.

We claim:

1. Compounds of N,N'-di(aralkyl)-N,N'-di(2-azaaralkyl) alkylene diamine, wherein said compounds correspond to the following general formula:

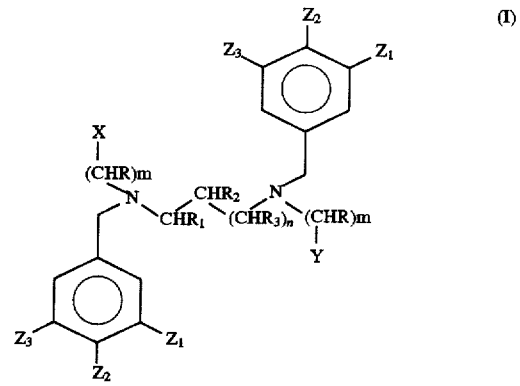

where:

n is 0, 1, or 2, m is 1, 2, or 3,

R, R$_1$, R$_2$, and R$_3$, whether identical or different, represent an atom of hydrogen or a linear or branched alkyl radical of C$_1$–C$_4$, R$_1$ and R$_2$, or R$_2$, and R$_3$ taken together can form a 5- or 6-membered ring, X and Y, whether identical or different, represent a nitrogenous aromatic heterocycle selected from the group consisting of 2-pyridyl, 2-pyrimidyl, 4-pyrimidyl, 2-triazinyl, 2-imidazolyl, 2-pyrrolyl, 2-tetrazolyl, 4-thiazolyl, 2-methy-4-thiazolyl and 2-benzoimidazolyl radical, Z$_1$, Z$_2$, and Z$_3$, whether identical or different, represent an atom of hydrogen, a linear or branched alkyl radical of C$_1$–C$_4$, the radical —OR$_4$ or —NR$_4$R'$_4$, R$_4$ and R'$_4$ represent an atom of hydrogen or a linear or branched alkyl radical of C$_1$–C$_4$ provided that one of Z$^1$, Z$^2$ and Z$^3$ is other than hydrogen, hydroxy or OR$^4$ where R$^4$ is hydrogen, and the salts and metallic complexes thereof.

2. Compounds according to claim 1, wherein the linear or branched alkyl radical is selected from the group consisting of methyl, ethyl, isopropyl and tertbutyl radicals.

3. Compounds according to claim 1, wherein at least one of the radicals Z$_1$, Z$_2$, and Z$_3$ represents a methoxy group.

4. Compounds according to claim 1, wherein the salts incorporate the addition of a mineral acid selected from the group consisting of sulfuric acid, chlorhydric acid, nitric acid, and phosphoric acid.

5. Compounds according to claim 1, wherein the complexes are formed by adding zinc chloride or calcium chloride.

6. Compounds according to claim 1, wherein said compounds are selected from the group consisting of:

N,N'-bis-(3,4,5-trimethoxybenzyl)-N,N'-bis-(2-tetrazolyl-1-ethyl) ethylenediamine, N,N'-bis(3,4,5-trimethoxybenzyl)-N,N'-bis-(2-pyridyl methyl) ethylenediamine, N,N'-bis-(2-methyl-thiazole-4-ylmethyl)-N,N'-bis-(3,4,5-trimethoxybenzyl) ethylenediamine, and N,N'-bis-(1H-benzoimidazole-2-ylmethyl)-N,N'-bis-(3,4,5-trimetehoxybenzyl) ethylenediamine.

7. Pharmaceutical or cosmetic composition, wherein said composition contains, in a pharmaceutically- or cosmetically-acceptable vehicle, at least one compound corresponding to formula (I) as claimed according to claim 1.

8. Composition according to claim 7, wherein said composition contains the compound corresponding to formula (I) in a proportion of 0.001 to 10% by weight of the total weight of the composition.

9. Composition according to claim 8, wherein it further contains at least one active ingredient selected from the group consisting of anti-lipoperoxidants, biological reductants, oxygen quenchers, enzymes, superoxide dismutase (SOD) or SOD-like substance, glutathion peroxidase, and selenium-based systems.

10. A method of treating at least one of oxidative stress or skin aging comprising administering to a mammal in need of such treatment a cosmetically- or pharmaceutically-acceptable dose of a compound of claim 1 in a cosmetically- or pharmaceutically-acceptable carrier.

UNITED STATES PATENT AND TRADEMARK OFFICE

CERTIFICATE OF CORRECTION

PATENT NO.      : 5,760,037
DATED           : June 2, 1998
INVENTOR(S)     : GALEY It is certified that error appears in the above-identified patent and that said letters patent is hereby corrected as shown below:

Column 8, lines 40-41, delete "provided that one of $Z^1$, $Z^2$, and $Z^3$, is other than hydrogen or hydroxy or $OR^4$ where $R^4$ is hydrogen" and insert --provided that one of $Z_1$, $Z_2$, and $Z_3$ is other than hydrogen or $OR_4$, $R_4$ being an atom of hydrogen--.

Signed and Sealed this

Twenty-third Day of March, 1999

Attest:

Q. TODD DICKINSON

*Attesting Officer*    *Acting Commissioner of Patents and Trademarks*